United States Patent [19]

Baumann et al.

[11] Patent Number: 4,477,923
[45] Date of Patent: Oct. 16, 1984

[54] X-RAY DIAGNOSTIC SYSTEM FOR ANGIOGRAPHIC RADIOGRAPHS

[75] Inventors: Heinz Baumann, Uttenreuth; Hans-Jürgen Gerlach, Erlangen, both of Fed. Rep. of Germany

[73] Assignee: Siemens Aktiengesellschaft, Berlin and Munich, Fed. Rep. of Germany

[21] Appl. No.: 425,315

[22] Filed: Sep. 28, 1982

[30] Foreign Application Priority Data

Feb. 3, 1982 [DE] Fed. Rep. of Germany ....... 3203594

[51] Int. Cl.³ .............................................. G03B 41/16
[52] U.S. Cl. .......................................... 378/95; 378/99
[58] Field of Search ................................ 378/95, 99, 8

[56] References Cited

U.S. PATENT DOCUMENTS 4,185,198 1/1980 Fujimoto ............................... 378/95

OTHER PUBLICATIONS

Holik, V. B. "Methode zur Vermeidung der Fehlprogrammierung bei der Becken–Bein–Angiographie mit schrittweiser Tischplattenverschiebung", *Electromedica*, 1/1977, pp. 2 through 6.

*Primary Examiner*—Craig E. Church
*Attorney, Agent, or Firm*—Hill, Van Santen, Steadman & Simpson

[57] ABSTRACT

An exemplary embodiment comprises a patient support, an x-ray tube supplied by an x-ray generator, an x-ray image intensifier with a series connected television chain, a control loop for the controlling the mean image brightness, a syringe for contrast medium injection, and a program memory for storing several radiographic exposure programs. A time measuring device is present which is started by the syringe and is stopped by an evaluation unit when the mean image brightness varies to a predetermined extent. A computer calculates the contrast medium velocity from the measured time and the distance (x) between the injection location and the measuring location. On the basis of the calculated contrast medium velocity, an optimum program calculation, or program selection, respectively, is possible.

6 Claims, 4 Drawing Figures

X-RAY DIAGNOSTIC SYSTEM FOR ANGIOGRAPHIC RADIOGRAPHS

BACKGROUND OF THE INVENTION

The invention relates to an x-ray diagnostic system for angiographic radiographs, comprising a patient support, an x-ray tube, arranged on one side of the support, supplied by an x-ray high voltage generator, an x-ray image intensifier, arranged on the other side of the support, with an associated television chain, a control loop for controlling the mean image brightness, and a syringe for contrast medium injection.

An x-ray diagnostic system of this type is described in the journal "Electromedica", 1/1977, on pages 2 through 6. Regarding this known x-ray diagnostic system, for the purpose of avoiding false estimations of the contrast medium flow velocity, and hence for the purpose of avoiding a faulty program selection, the proposal is made that the contrast medium velocity be measured and, on the basis of the measured value, the respectively optimum program be selected. The measurement of the contrast medium velocity proceeds in such a manner that the time is detected which the contrast medium requires to travel from the injection location to a specific measuring location, for example lying in the knee region, and that from such time measurement, and from the distance between the injection location and measuring location, the contrast medium velocity is calculated.

SUMMARY OF THE INVENTION

The object underlying the invention resides in producing an x-ray diagnostic system of the type initially cited in which an automatic determination of the contrast medium velocity takes place, and in particular an electric signal corresponding to said velocity is automatically generated.

This object is achieved in accordance with the invention by means of a time measuring device capable of being started by the syringe, which device is stopped by an evaluation unit when the mean image brightness varies by a predetermined amount, and by means of a computer for calculating the contrast medium velocity from the measured time and the distance between the injection location and the measuring location. In the case of the inventive x-ray diagnostic system, with the aid of the control loop for the mean image brightness, an electric signal can be formed at the measuring location which preferably lies in the knee region, which signal characterizes the arrival of the contrast medium at the measuring location. With this arrival, namely, the mean image brightness varies downwardly, so that also the output signal of the sensor for the mean image brightness, which is preferably a photomultiplier, varies by a predetermined amount. This change can be detected in the evaluation unit and employed for the automatic time measurement.

An expedient embodiment of the invention is one wherein a signal corresponding to the calculated velocity is supplied to the program memory for the purpose of automatic program selection, and display means for displaying the respective selected program are present. In the case of this embodiment, the program selection proceeds automatically, although the physician nevertheless has the option of departing from the adjusted and displayed value.

The invention shall be explained in greater detail in the following on the basis of an exemplary embodiment illustrated on the accompanying drawing sheet; and other objects, features and advantages will be apparent from this detailed disclosure and from the appended claims.

DETAILED DESCRIPTION

Figure 1:
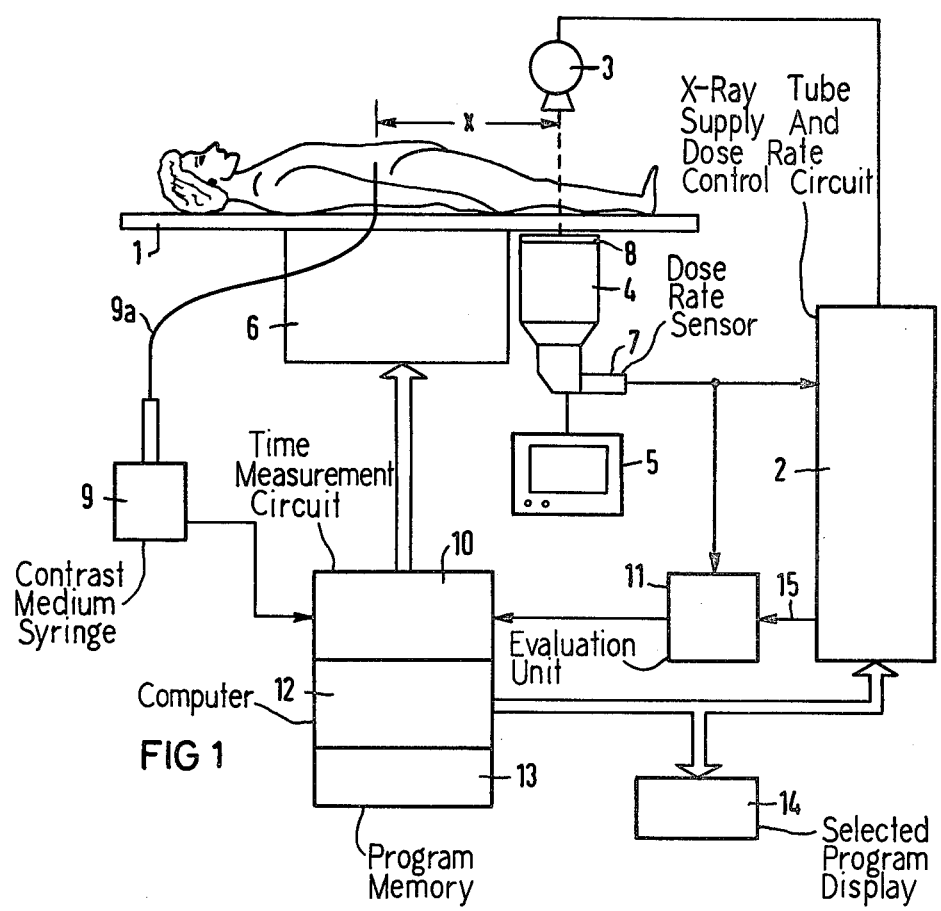
FIG. 1 illustrates an x-ray diagnostic system according to the invention.

In FIG. 1, a patient support 1 is illustrated on the one side of which an x-ray tube 3, supplied by an x-ray high voltage generator 2, is arranged, and on the other side of which, an x-ray image intensifier 4 is disposed with which a television chain with a display unit 5 is series connected. The patient support 1 rests on a base 6 and is longitudinally displaceable relative to said base 6 by motor means. The x-ray image intensifier 4 permits fluoroscopy of a region of the patient. A control of the mean image brightness on the display unit 5 thus takes place with the aid of a photomultipler 7 as actual value transmitter. The comparator and controller of the control loop are component parts of the x-ray generator 2. The image brightness is kept constant through alteration of the dose rate of the x-ray tube 3 via the x-ray tube current and/or the x-ray tube voltage. For the preparation of radiographs, a film changer 8 is present.

For angiographic radiographs, a contrast medium syringe 9 is present which is connected to the patient with the aid of a tube 9a and a catheter arranged at the end of the tube 9a. The contrast medium syringe starts a time measuring device 10 which is stopped by the output signal of an evaluation unit 11. A computer 12 serves the purpose of determining the contrast medium velocity and selects, corresponding to the computed velocity, a radiographic program from a program memory 13 and effects adjustment in the x-ray generator 2 and the corresponding control of the table movement in accordance with the selected program during the angiographic examination. A display device 14 indicates the respectively selected radiographic program.

Figure 2:
FIGS. 2 through 4 illustrate a timing diagram for the purpose of explaining FIG. 1.

For the preparation of a photographic series of angiographic radiographs, first a sample injection of contrast medium in the patient is conducted. At the time t0, for this purpose, the contrast medium syringe 9 is activated and supplies to the time measuring device 10 a start signal which determines the beginning of a time measurement The contrast medium injection is terminated at the time tl (FIG. 2). Prior to the contrast medium injection, a fluoroscopic operation has already been initiated and the control loop for the mean image brightness has been activated. After adjustment of the control loop, there is supplied to the evaluation unit 11, by the x-ray generator 2, on the line 15, a signal corresponding to the mean image brightness, referenced in FIG. 4 with 100%.

As soon as the contrast medium reaches the region in which fluoroscopy is taking place—in the example, the knee region—the mean image brightness initially varies by a predetermined percentage amount and it is some time until this change has been compensated for by the control loop. This fact is apparent from FIG. 4. The evaluation unit 11 is so programmed that, when a change of the mean image brightness —characteristic of the arrival of the contrast medium—occurs—in the example, by 5% downwardly, the time measuring device is stopped (time t2 in FIG. 3). In the time measuring device 10 now the time is stored which the contrast medium requires for flow from the injection location (abdominal region) to the measuring location (knee region). The distance between these two regions is designated in FIG. 1 with x. The computer 12 can calculate, from this distance and the time ($\Delta t$) stored in the time measuring device 10, the contrast medium velocity, and can recall a program corresponding to the calculated velocity from the program memory 13. The program can also be calculated directly by the computer 12 on the basis of the data for the image rate and number of images input by the physician. The physician can adopt or modify the calculated program.

The selected program of the program memory 13 contains, in particular, commands for the step displacement of the support at appropriate intervals, the times of the photograph triggerings, and the optimum contrast medium quantity for the actual contrast medium examination following the described sample examination.

Figure 3:
Figure 4:

From the above description, it is apparent that FIG. 2 shows the chronological progression of the syringe actuation; FIG. 3 shows that of the time measurement in the time measuring device 10; and FIG. 4 shows the output signal of the photomultiplier 7 as a function of time.

It will be apparent that many modifications and variations may be made without departing from the scope of the teachings and concepts of the present invention.

We claim as our invention:

1. An x-ray diagnostic system for angiographic radiographs, comprising a patient support, an x-ray tube, arranged on one side of the support, an x-ray high voltage generator supplying said x-ray tube, an x-ray image intensifer, arranged on the other side of the support, a television chain connected with the x-ray image intensifier, a control loop for controlling the mean brightness, and a syringe for contrast medium injection, characterized by a time measuring means, capable of being started by the syringe, an evaluation unit coupled with the time measuring means and operable for signalling the time measuring means when the mean image brightness varies to a predetermined extent, and characterized by a computer means for the determination of the contrast medium velocity from the measured time and from the distance between the injection location and the measuring location.

2. An x-ray diagnostic system according to claim 1, characterized in that a program memory is present for storing several exposure programs and is controlled by the computer means in accordance with the calculated velocity for the purpose of automatic program selection, and that display means for the respectively selected program are present.

3. An x-ray diagnostic system for controlling angiographic imaging, said system comprising a patient support, an x-ray tube arranged on one side of the support, an x-ray tube supply circuit for supplying said x-ray tube, x-ray image sensing means arranged on the other side of the support for sensing an x-ray image produced by said x-ray tube at a sensing location, and having an output for supplying an output image signal having a mean image brightness, a control loop comprising a dose rate sensor coupled with the output of the x-ray image sensing means for sensing the mean image brightness of the output image signal, said control loop being coupled with said x-ray tube supply circuit to tend to maintain the mean image brightness of the output image signal constant during an imaging operation, syringe means for injecting contrast medium at a contrast medium injection location, time measuring means coupled with said syringe means for initiating a time measurement operation when a contrast medium is injected into a patient at a contrast medium injection location, an evaluation unit having an input coupled with said dose rate sensor and having an output controlling said time measuring means and serving to terminate a time measurement operation when the evaluation unit senses a transient in the output of said dose rate sensor due to the arrival of the contrast medium at the sensing location of said x-ray image sensing means to produce a resultant time measurement of the time measuring means serving to characterize the contrast medium velocity in conjunction with the distance between the contrast medium injection location and the sensing location of said x-ray image sensing means.

4. An x-ray diagnostic system according to claim 3, with said dose rate sensor comprising a photomultiplier.

5. An x-ray diagnostic system according to claim 3, with said control loop operating such that the mean image brightness as sensed by said dose rate sensor is momentarily reduced by at least about five percent when the contrast medium reaches the sensing location of said x-ray image sensing means.

6. An x-ray diagnostic system for controlling angiographic imaging, said system comprising a patient support, an x-ray tube arranged on one side of the support, an x-ray tube supply circuit for supplying said x-ray tube, x-ray image sensing means arranged on the other side of the support for sensing an x-ray image produced by said x-ray tube at a sensing location, and having an output for supplying an output image signal having a mean image brightness, a control loop comprising a dose rate sensor coupled with the output of the x-ray image sensing means for sensing the mean image brightness of the output image signal, said control loop being coupled with said x-ray tube supply circuit to tend to maintain the mean image brightness of the output image signal constant during an imaging operation, syringe means for injecting contrast medium at a contrast medium injection location, time measuring means coupled with said syringe means for initiating a time measurement operation when a contrast medium is injected into a patient at a contast medium injection location, an evaluation unit having an input coupled with the output image signal from the x-ray image sensing means and operative for sensing an abrupt change in the output image signal due to the arrival of the contrast medium at said sensing location of said x-ray image sensing means, said evaluation unit having an output controlling said time measuring means and serving to terminate a time measurement operation when the evaluation unit senses an abrupt change in the output image signal to produce a resultant time measurement serving to characterize the contrast medium velocity in conjunction with the distance between the contrast medium injection location and the sensing location of said x-ray image sensing means.

* * * * *